(12) United States Patent
Arnold

(10) Patent No.: US 9,556,142 B2
(45) Date of Patent: Jan. 31, 2017

(54) PROCESS FOR THE PREPARATION OF (R,S)-NICOTINE

(71) Applicant: Next Generation Labs, LLC, San Diego, CA (US)

(72) Inventor: Michael Arnold, Beverly Hills, CA (US)

(73) Assignee: NEXT GENERATION LABS, LLC, San Diego, CA (US)

(*) Notice: Subject to any disclaimer, the term of this patent is extended or adjusted under 35 U.S.C. 154(b) by 0 days.

(21) Appl. No.: 14/920,796

(22) Filed: Oct. 22, 2015

(65) Prior Publication Data

US 2016/0115150 A1  Apr. 28, 2016

Related U.S. Application Data

(60) Provisional application No. 62/067,196, filed on Oct. 22, 2014.

(51) Int. Cl.
*C07D 401/04* (2006.01)

(52) U.S. Cl.
CPC ................... *C07D 401/04* (2013.01)

(58) Field of Classification Search
CPC .................................................... C07D 401/04
USPC ....................................................... 546/279.4
See application file for complete search history.

(56) References Cited

U.S. PATENT DOCUMENTS

| | | | | |
|---|---|---|---|---|
| 6,881,738 B2* | 4/2005 | Buccafusco | .......... | C07C 215/08 514/252.12 |
| 8,367,837 B2* | 2/2013 | Divi | .................... | C07D 401/04 546/279.4 |

FOREIGN PATENT DOCUMENTS

EP   2487172 A1   8/2012

OTHER PUBLICATIONS

Lloyd et al., "Pyrrolidine amides, etc.,", Bioorganic & Medicinal Chemistry Letters 20 (2010) 1436-1439.*

* cited by examiner

*Primary Examiner* — Patricia L Morris
(74) *Attorney, Agent, or Firm* — Lewis Roca Rothgerber Christie LLP

(57) ABSTRACT

A method of preparing (R,S)-nicotine, comprising reacting a nicotinate ester with N-vinyl-2-pyrrolidinone in the presence of a base and a solvent to form a first mixture, combining the first mixture with an acid to form a second mixture comprising an aqueous layer, separating the aqueous layer from second mixture, combining the separated aqueous layer with an acid to form a third mixture, combining the third mixture with a base to form a fourth mixture comprising myosamine, reducing myosamine to nornicotine using a reducing agent, and methylating the nornicotine to yield R,S-nicotine.

20 Claims, No Drawings

PROCESS FOR THE PREPARATION OF (R,S)-NICOTINE

CROSS REFERENCE TO RELATED APPLICATION

This application claims priority to U.S. Provisional Application No. 62/067,196, filed Oct. 22, 2014, entitled "PROCESS FOR PREPARATION OF (R,S) NICOTINE," the entirety of which is hereby expressly incorporated by reference herein.

FIELD OF THE INVENTION

The present invention relates to the field of synthetic methodology for the large scale manufacturing of pure (R,S)-nicotine, and its use in vapor for treatment of tobacco smoking cessation and/or recreational use.

BACKGROUND OF THE INVENTION

Nicotine is currently used as a dilute solution, typically in combination flavor, in liquid in vaporization devises (commonly known as vaporizers), as well as cessation devises such as patches and gums. A salient feature of the state of the art is that essentially all the nicotine employed in these "vaping devises" is nicotine liquor that has been prepared from tobacco, extracted from the tobacco plant usually using kerosene as the solvent, then purified; and such extracts cannot be purified to rid of many of the compounds that are also found in tobacco plant extract. Thus, extremely pure nicotine that is devoid of these contaminants is not, nor has not been commercially available, and may prove to be very difficult to prepare commercially, or even in research quantities. It is important to note that many of these contaminants are unhealthful for the human system, many have been shown to be carcinogenic, and enhance addictive qualities of the "nicotine".

A need for nicotine material that is devoid of these disease causing contaminants exist in today's marketplace.

While several synthetic methods of nicotine preparation are known, the commercialization of synthetic nicotine has not taken place. Known methods of preparing extremely pure synthetic nicotine are prohibitively costly on an industrial scale. See for example, EP 2487172.

Thus, there is a need in the art for a synthesis of nicotine that avoids/minimizes many of the pitfalls of the methods previously reported for the synthetic preparation of nicotine on an industrial scale, thus achieving pure nicotine in commercially viable quantities and with an acceptable cost of manufacturing.

SUMMARY OF THE INVENTION

Aspects of the present invention includes a method of preparing (R,S)-nicotine, comprising reacting a nicotinate ester with N-vinyl-2-pyrrolidinone in the presence of a base and a solvent to form a first mixture, combining the first mixture with an acid to form a second mixture comprising an aqueous layer, separating the aqueous layer from second mixture, combining the separated aqueous layer with an acid to form a third mixture, combining the third mixture with a base to form a fourth mixture comprising myosamine, reducing myosamine to nornicotine using a reducing agent, and methylating the nornicotine to yield R,S-nicotine.

DETAILED DESCRIPTION OF THE INVENTION

The present invention overcomes many of the pitfalls of the prior art by providing for a cost-effective method for the preparation of pure (R,S)-Nicotine that is devoid of all, or most of the carcinogenic congers of tobacco derived nicotine.

An aspect of the present invention provides for a synthesis of pharmaceutically pure, USP grade, (R,S) Nicotine that is applicable for an industrial scale preparation that is commercially viable. Another aspect of the present invention provides for a method for synthesis of pharmaceutically pure nicotine that is devoid of most of, or any of the other non-nicotine moieties commonly found in tobacco-derived nicotine. Another aspect of the present invention provides for RS-Nicotine preparations that are greater than 99.5% pure and that meet or surpass the purity requirements described for Nicotine in the United States of America USP monograph. Another aspect of the present invention provides for a synthetic route to RS-Nicotine that utilizes starting materials that are readily available in large quantities, worldwide, and that are of a cost to the producer that allows for favorable pricing to the wholesale marketplace, competitive with tobacco-derived Nicotine.

A diagram of the general synthetic method of the present invention is outlined in Scheme 1.

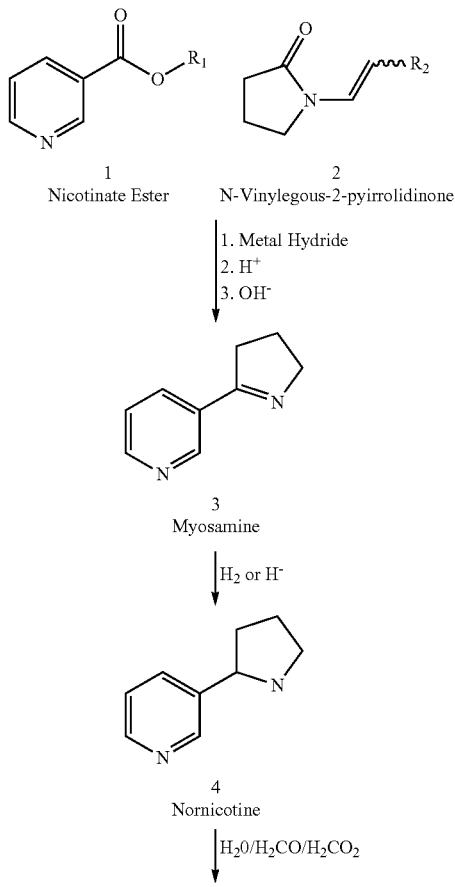

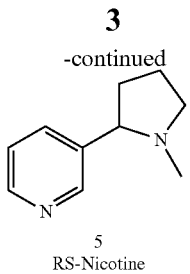

RS-Nicotine

The preferred synthetic route comprises as a first step a carbon-carbon bond forming condensation performed under anhydrous conditions. The materials for this first reaction mixture that are an appropriate nicotinate ester (1) and this is condensed with a suitable N-vinylogous-2-pyrrolidinone (2) under mild conditions, utilizing a suitable dry solvent in combination with a suitable strong base, typically a metal hydride. This first step gives excellent yields of the condensation adduct (as its metal salt).

In some embodiments, the reaction mixture utilizes alkyl esters of nicotinic acid in combination with N-vinyl-2-pyrrolidinone, and metal hydride base in suitable dry solvent. In some embodiments, the nicotinate alkyl ester comprises short chain alkyl groups (preferably R1 is $C_{1-3}$, and more preferably $C_2$). The preferred n-vinyligous-2-pyrrolidinones comprise a vinyl substituent with a short chain alkyl group. In some embodiments, R2 is a short chain ($C_{1-10}$) alkyl (such as methyl, isopropyl, etc.), or in some preferred embodiments, $R_2$ is hydrogen (H). In some preferred embodiments, the n-vinyligous-2-pyrrolidinones is n-vinyl-2-pyrrolidinone.

The amount (relative moles) of metal hydride utilized in the First Reaction Mixture with respect to 1 part nicotinate ester is from about 0.1 part to about 2.5 parts, more preferably from about 1.2 parts to about 2.1 parts, and most preferably from about 1.8 parts to about 2 parts, and where the mole ratio of metal hydride to nicotinate ester is from about 1 to 4, preferably from about 1:2 to about 1.6:2, and most preferably 2:2. The preferred metals are lithium, potassium or sodium, the more preferred are potassium or sodium, and the most preferred is sodium.

The amount of N-vinylogous-2-pyrolidinone with respect to the amount (mole equivalents) of nicotinate ester in the First Reaction Mixture is from about 0.1 parts to about 10 parts, more preferably from about 0.5 parts to about 3 parts, and most preferably from about 1.0 parts to about 1.2 parts.

The amount of solvent in this First Reaction Mixture with respect to 1 part (mole equivalents) nicotinate ester is from about 1 parts to about 15 parts, preferably from about 3 parts to about 10 parts, more preferably from about 4 parts to about 8 parts and most preferably from about 5 parts to about 7 parts of the total reaction mixture. The preferred solvents are anhydrous. Dipolar aprotic solvents such as Dimethylformamide (DMF) are useful in the present invention. Ethers may also be employed, ethyl ether, tetrahydrofuran (THF), or tetrahydrofuran derivatives, polyethers such as "glyme" or "diglyme" may also be employed, and combinations of these solvents may also be utilized in the First Reaction Mixture. Aromatic hydrocarbons, or hydrocarbon solvents may also be employed in an aspect of the present invention as solvents for the First Reaction Mixture; toluene, xylenes, benzene are the preferred aromatic hydrocarbon solvents for the First Reaction mixture. A preferred solvent for the first reaction mixture is an alcohol, or an alcohol and ether combination, another preferred solvent is THF, or a Mixture of DMF and ether, and/or a mixture of DMF and hydrocarbon or aromatic hydrocarbon, and the most preferred solvent is toluene (or benzene). Alcohols such as ethanol, methanol, propanol may be added to help catalyze the first step, or used as the only solvent. If alcohol is to be used as a solvent or co-solvent in the First Reaction Mixture, then the metals sodium, potassium or lithium may be employed in less than or equal to stoichiometric amounts with respect to the Nicotinate ester. A preferred time of addition is such that a mild effervescence is maintained, and an internal temperature of between 50° C. and 80° C. is maintained throughout the addition process. The time of addition varies with Volume, but usually takes place within a matter of minutes to hours. After addition of the Nicotinate Ester solution, the greenish First Reaction Mixture is stirred, preferably under an inert atmosphere an appropriate amount of time in order to complete the reaction. The preferred method has this First Reaction Mixture heated to in internal temperature from about 40° C. to about 110° C., more preferably from about 60° C. to about 100° C., and most preferably from about 80° C. to about 95° C.

Prior to the second step, and after reacting nicotinate ester with N-vinylogous-2-pyrrolidinone, the First Reaction Mixture contains any unreacted starting material (nicotinate ester, n-vinylogous-2-pyrrolidinone, sodium hydride) as well as reaction products: the main condensation product which is the nicotinate-n-vinylogous-2-pyrrolidinone adduct (the condensation adduct, an organic bicyclic compound as the metal salt, e.g., 1-(1-alkenyl)-3-nicotinoylpyrrolidine-2-one, preferably where the alkenyl is ethenyl), the alcohol as the metal salt, and some alcohol that is displaced from the nicotinate ester as the alcohol.

As a second step, after completion of the reaction that takes place as a result of the action of the First Reaction Mixture, this reaction product mixture is either injected (or poured) directly into a solution of acid to form a Second Reaction Mixture. This can be done with boiling acid solution, or into cold acid aqueous solution. The preferred acid is aqueous hydrochloric acid solution. The preferred normality of the acid solution is from about 3-12, more preferred from about 4-7, and most preferred from about 5-6.

A preferred method for the Second Reaction Mixture has the completed First Reaction Mixture, cooled to ambient temperature and then injected into a cold solution of acid. The amount of the acid is from about 0.25 parts to about 5 parts, more preferably from about 0.5 parts to about 2 parts, and most preferably from abut 0.75 parts to about 1.5 parts with respect on part of the First Reaction Mixture.

The action of the Second Reaction Mixture yields a biphasic mixture where the protonated bicyclic pyridine-pyrrolidinone adduct (i.e., protonated condensation adduct) which is soluble in water and insoluble in the organic solvent is present, and any unreacted pyrrolidinone starting material is in the organic layer. When the reaction is let settle with no agitation, two distinct layers are formed, aqueous and organic (non-aqueous), the product of the reaction is in the aqueous layer, and this aqueous layer is then separated and subjected to the next step.

After the acid addition, then the aqueous and organic (non-aqueous) layers are separated, a concentrated acid is added to the separated aqueous layer to form a Third Reaction Mixture. This Third Reaction Mixture is then heated to reflux for an appropriate period of time to complete the reaction.

The amount of concentrated acid added to this Second Reaction Mixture to form the Third Reaction Mixture is from about 0.15 parts to about 1.5 part, more preferably from about 0.2 part to about 0.5 part, and most preferably from about 0.25 part to about 0.5 part with respect to 1 part Second Reaction Mixture. The preferred acid is 12N hydrochloric acid (concentrated hydrochloric acid [ca37%]).

After the reaction of the Third Reaction Mixture is complete, this mixture is comprised of water, acid, and product as the protonated acyclic amine salt, e.g., protonated 3-(4-aminobutanyl-1-one)-pyridine.

After the reaction of the Third Reaction Mixture is complete, it is cooled to between −10° C. and 5° C. then this acidic solution is made strongly basic (pH>9) while keeping the temperature at an appropriate level, and the result is the Fourth Reaction Mixture, which is comprised of, at completion of this step, Myosamine, base, water, and any remaining unreacted material from the Third Reaction Mixture, as well as contaminants natural to the reaction. The resulting basic aqueous composition comprises a Fourth Reaction Mixture, and is extracted thoroughly with organic solvent, and then the solvent distilled off to yield crude Myosamine. The preferred organic solvent is dichloromethane. The preferred amount of organic solvent is from about 1 part to about 10 parts with respect to the amount of the Fourth Reaction Mixture, preferably from about 1.5 parts to about 5 parts, and most preferably from about 2 parts to about 4 parts with respect to the basic Fourth Reaction Mixture.

An alternative method has the completed First Reaction Mixture injected directly into a hot solution of hydrochloric acid, and the resulting heterogeneous mixture comprises the Second Reaction Mixture. This mixture is heated with an external bath to enable vigorous reflux, and where such vigorous reflux is continued until the reaction is complete. For this alternative method of the second step, the preferred solvent for the First Reaction Mixture is toluene or xylene, or high boiling solvent such as diglyme.

A Fifth Reaction Mixture is prepared in order to reduce the crude Myosamine product to form crude Nornicotine product. The Fifth Reaction Mixture is prepared by added a suitable hydrogenation catalyst in a suitable amount to the crude Myosamine (3) in solution with an appropriate solvent. To complete the reduction of Myosamine to Nornicotine, this Fifth Reaction Mixture is submitted to an atmosphere of hydrogen gas at a pressure greater than or equal to ambient pressure, but not high enough to reduce the carbons in the pyridine ring.

The preferred solvent for the Fifth Reaction Mixture is an alcoholic solvent, most preferred is ethanol or isopropanol, although other solvents known to the art of hydrogenation can be employed. The amount of solvent is from 3 parts 98 parts, more preferably from about 4 parts to about 60 parts, and most preferably from about 5 part to about 20 parts solvent with respect to 1 part crude Myosamine. The preferred catalyst is 10% palladium on carbon, but other catalyst common to the art of catalytic hydrogenation may also be employed, either as a co-catalyst, or not. The pressure of the hydrogen gas can be from ambient to about 100 atmospheres hydrogen, more preferably from about ambient to about 75 atmospheres, and the most preferred is from about 10-50 atmospheres hydrogen.

An alternative to the Fifth Reaction Mixture utilizes a borohydride salt for the reducing agent rather than catalytic hydrogenation, and different reaction conditions.

At the completion of the reaction of the Fifth Reaction Mixture, this mixture is comprised of Nornicotine (reduction product), catalyst and solvent, as well as any unreacted starting material (crude Myosamine) and contaminating reaction unwanted products.

A Sixth Reaction Mixture is formed upon addition of water, Formic acid and Formaldehyde to the crude Nornicotine (4) product from the Fifth Reaction Mixture. This Sixth Reaction Mixture is heated to an appropriate temperature for a duration which allows for the completion of the methylation reaction to afford crude Nicotine in good yields.

At the completion of the reaction of the Sixth Reaction Mixture, such a mixture contains crude RS-Nicotine product, solvent (water), and any unreacted starting material including formaldehyde and formic acid, as well as reaction contaminating by-products.

The product of the Sixth Reaction Mixture, crude RS-Nicotine (5), is subjected to at least one high vacuum distillation to give pure (greater than 95% pure, more preferably greater than 97% pure, more preferably greater than 99% pure, and more preferably greater than 99.5% pure) RS-Nicotine as a clear, colorless non-viscous liquor in good to excellent overall yields.

EXAMPLE 1

To a stirred solution of 1-vinyl-2-pyrrolidinone (2) in dry THF under a nitrogen atmosphere was added 1 equivalent of potassium hydride. The reaction was let stir at room temperature for about 20 minutes, then ethyl nicotinate (1 equivalent) was added and the resulting mixture stirred 24 hours at 65 degrees centigrade. The reaction was cooled and then acidified with 5% HCl and then concentrated HCl was added and this was then refluxed for 48 hours. The pH was adjusted to 13 with sodium hydroxide, and then 3× equal volume of dichloromethane was added and each time the layers were separated and the combined extracts dried over sodium sulfate, filtered and the solvent evaporated to give amorphous material. This was taken up in 3 parts ethanol was then added, and then palladium on carbon was added (cas 10%) and the resulting mixture was submitted to hydrogen pressure for 6 hours (greater than 25 atmospheres), and then the residue was diluted with more ethanol and filtered through celite. The solvent was evaporated under vacuum with minimal heat, to dryness, and then the residue was taken up in formic acid/formaldehyde solution (1:1) and the resulting mixture heated to 90 degrees Celsius for 12 hours, and then cooled and neutralized with sodium hydroxide to pH>10, and then extracted with dichloromethane and then dried over sodium sulfate, filtered and concentrated to give brown oil. This oil was vacuum distilled to give pure RS Nicotine.

EXAMPLE 2

To a stirred solution of 1-vinyl-2-pyrrolidinone (2) in dry THF/DMF (3/1) under a nitrogen atmosphere was added 1.2 equivalent of sodium hydride. The reaction was let stir at room temperature for about 20 minutes, then ethyl nicotinate (1) (1 equivalent) was added and the resulting mixture stirred 24 hours at 65 degrees centigrade. The reaction was cooled and then acidified with 5% HCl and then to this was added concentrated HCl, and the resulting mixture refluxed for 48 hours. The pH was adjusted to 6 and then excess dichlormethane was added and the layers separated. The aqueous layer was extracted twice with excess dichlormethane, and the extracts combined and washed with water, then dried over sodium sulfate. The solution was then filtered and the solvent removed using vacuum to yield a brownish solid. This solid was dissolved in ethanol (ca 5-10 parts) and then 0.5 part palladium on carbon was added and the resulting mixture was submitted to hydrogen pressure for 6 hours (greater than 25 atmospheres), and then the residue was diluted with more ethanol and filtered through celite. The solvent was evaporated under vacuum with minimal heat, to dryness, and then the residue was taken up 3 parts formic acid and 3 parts formaldehyde, and the resulting solution heated to 100 degrees centigrade for 24 hours. The reaction was cooled and then vacume distilled to yield pure RS nicotine (5) as a clear, colorless non-viscous oil.

EXAMPLE 3

To a stirred solution of 1-vinyl-2-pyrrolidinone (2) in dry DMF under a nitrogen atmosphere was added 1 equivalent of potassium hydride. The reaction was let stir at room temperature for about 20 minutes, then ethyl nicotinate (1 equivalent) was added and the resulting mixture stirred 24 hours at 65 degrees centigrade. The reaction was cooled and then acidified with 5% HCl and then refluxed for 48 hours. The pH was adjusted to 6 and then an isopropanolic suspension of sodium borohydride was added in excess and the reaction let stir 24 hours at room temperature, then acidified to pH about 3 with 5% HCl, then stirred for about 15 minutes. 10 parts dichlormethane was added and the layers separated, the organic layer was dried over sodium sulfate, filtered and then 1.1 equivalent of potassium carbonate was added and then 1.1 equivalent of methyl iodide was added and the reaction let stir 24 hours, filtered and the solvent removed to yield an oil which was vacume distilled to yield pure RS nicotine.

EXAMPLE 4

To a stirred solution of 1-vinyl-2-pyrrolidinone (2) in dry THF under a nitrogen atmosphere was added 1 equivalent of potassium hydride. The reaction was let stir at room temperature for about 20 minutes, then ethyl nicotinate (1 equivalent) was added and the resulting mixture stirred 24 hours at 65 degrees centigrade. The reaction was cooled and then acidified with 5% HCl and then concentrated HCl was added and the resulting mixture refluxed for 48 hours. The pH was adjusted to 6 and then an isopropanolic suspension of sodium borohydride was added in excess and the reaction let stir 24 hours at room temperature. About 10 parts formic acid and about 10 parts formaldehyde was then added, and the resulting solution was stirred at about 100 degrees centigrade for 24 hours, cooled then brought to pH about 12 by addition of sodium hydroxide solution, then the layers were separated and the aqueous layer washed many times with dichloromethane. The organic extracts were dried over sodium sulfate and the solvent removed and the resulting crude oil vacuum distilled to yield pure RS nicotine as a clear and colorless non viscous liquor.

EXAMPLE 5

To a stirred solution of 1-vinyl-2-pyrrolidinone (2) in toluene was added 1.2 equivalents of sodium hydride (60% dispersion in oil), and to this was added drop-wise over 20 min a concentrated solution of ethyl nicotinate (1 equivalent) in toluene, and the resulting mixture heated to reflux for 3 hours. This crude reaction mixture was cooled in an ice bath, and then excess concentrated hydrochloric acid was added and the resulting solution heated to 85-110 Celsius for 12 hours, and then cooled to room temperature, and then the upper toluene layer removed. To the acidic aqueous layer wan added sodium hydroxide until the pH was over 12, and then adjusted to about 8 with HCl, and to this stirred solution was added 2.5 equivalents of sodium borohydride solution in isopropanol (stabilized with sodium hydroxide), and the resulting mixture let stir for 6 hours (until completion), and then to this was added excess formic acid and formaldehyde, and the resulting mixture was refluxed for 10 hours, and then brought to neutral or slightly basic pH, and then the solvents were removed by vacuum and then the remaining residue was vacuumed distilled to yield pure R,S, Nicotine (bp=74-76 degrees Celsius @ 0.5 mmHg).

EXAMPLE 6

Synthesis of Myosamine: Sodium hydride (1.25 Kg, 31.2 mole) was added to a stirred solution of toluene (10 L) under inert atmosphere (dry nitrogen or argon gas) and this was let stir for about 15 minutes at room temperature. Then, a solution of n-vinyl pyrrolidinone (2 kg, 18.02 mole) in 1 L of toluene was added over 15 minutes via addition funnel, and the resulting mixture let stir at ambient temperature for about 15 minutes. Then a solution of ethyl nicotinate (2.5 Kg, 16.56 mole) in 2 L toluene was added in portions over a two hour period. The mildly effervescent exothermic reaction mixture turned a light rose color and then a light green ppt formed as the exothermic reaction maintained itself at about 60-65° C. After addition was complete, the reaction mixture was heated to 85° C. for about 16 hours, then cooled to room temperature yielding a greenish heterogeneous mixture. (NOTE: this mixture is flows well and is able to be pumped through ½" PE tubing with diaphragm pump with facility.) This mixture is added, in about 250 mL portions, to 25 L of a boiling solution of 6N HCl. (NOTE: The addition takes place with vigorous effervescence, which subsides within a few minutes after addition of the aliquot of reaction mixture to the hot HCl.) After all the reaction mixture has been added, the resulting dark brown biphasic mixture was stirred under reflux for an additional hour. Then, the reaction was cooled, and the layers separated. The aqueous layer was cooled, and made basic (pH>10) with NaOH (50%), then extracted 3×8 L of dichloromethane, and the solvent removed via vacuum distillation (T bath=ca.45 degrees centigrade) to yield a dark brown, non-viscous oil.

Synthesis of Nornicotine: The total crude Myosamine (from above) was taken up in 16 L ethanol, and 250 grams of 10% palladium on carbon was added and then resulting mixture, was stirred under hydrogen atmosphere for 12 hours, then filtered using celite, and washed with ethanol. The ethanol was removed using vacuum to give a dark brown non-viscous oil RS-Nicotine: Synthesis of RS Nicotine: To the crude Nornicotine was added 2.0 Kg of formaldehyde (37%) and 1.5 Kg of formic acid (85%), and the resulting brown solution was heated to an internal temperature of 85 degrees centigrade for 15 hours, then cooled to ambient temperature. This chilled to about 5 degrees centigrade, and then was made basic by addition of NaOH. This was then extracted 3×8 L of dichloromethane, and the solvent removed by vacuum. Pure nicotine was obtained using high vacuum distillation (75-76 @0.5 mmHg) to yield a clear, colorless non-viscous oil (ca31% overall yield from ethyl nicotinate).

An alternative Nornicotine preparation from Myosamine is provide below.

Synthesis of Nornicotine—METHOD B. The total crude Myosamine (from above) was taken up in 16 L methanol and 4 L of acetic acid, and the resulting solution was cooled to an internal temperature of −40 degrees centigrade, then 700 grams of sodium borohydride (granular) was added in portions over 1 hour. The reaction was let warm to room temperature with stirring, and then submitted to vacuum distillation to remove most of the solvent. The resulting liquor was added 25 L of water. This was brought to pH>10 with NaOH. This was extracted three times with 15 L of dichloromethane, and the combined extracts were submitted to medium vacuum distillation to give a crude non-viscous dark brown colored oil.

EXAMPLE 7

An alternative to first step in the multi-step sequence of reactions is described below.

Similar to previous acidification of the First Reaction Mixture, but rather than shoot initial reaction mixture directly into hot acid solution, this uses a milder method where the completed First Reaction Mixture is injected into cold acid to quench the reaction, then a Second Reaction Mixture is prepared.

To 2.5 Kg of Sodium Hydride (60% dispersion in mineral oil) as a stirred suspension in 20 L of toluene is added a solution of N-vinyl pyrrolidinone (4.5 kg) in 2.5 Kg of toluene, and the resulting mixture was stirred for about 15 minutes at room temperature. To this was added, in portions and constant slow stream of liquor (light golden color), 5 Kg of ethyl nicotinate in 10 Kg of toluene, controlling the exothermic reaction at an internal temperature of about 60° C. by rate of addition of the ethyl nicotinate-toluene solution. This gives after about one third of the ethyl nicotinate was added a green ppt. After addition was complete, the green heterogeneous mixture was heated to 85° C. for about 12 hours. This was injected into a precooled solution of 30 L of 4NHCl at 0° C. followed by vigorous stirring for about 5 minutes. The layers were separated, and the toluene layer washed once with 2.5 Kg of 4NHCl. To the combined acidic aqueous layers was added 8 L of concentrated HCl, and the reaction heated to boiling for about 3 hours (or until reaction complete by TLC). The reaction was cooled to 0° C., and then neutralized with 50% sodium hydroxide solution while not letting the internal temperature to go above 35-40 degrees centigrade. The pH was made very basic by addition of sodium hydroxide solution (50%) until pH 11-13 (litmus paper blue). This was extracted 4×15 L with dichloromethane, and the combined extracts were subjected to medium vacuum distillation to yield a non-viscous brownish oil (Myosamine). To this crude Myosamine product was added 40 L of anhydrous ethanol, and this resulting solution was added 2 Kg of 10% palladium on carbon, and the resulting mixture was subjected to pressure of hydrogen of 50 atm. The reaction was comple within 12 hours. The heterogeneous mixture was filtered through celite, and then washed twice with 10 L of ethanol, and the combined ethanolic solution of the crude Nornicotine product was subjected to vacuum distillation (29 inches Hg) at below 50° C., and then the crude dark brown oil was taken up in 10 L water, and to this was added a solution of 5 L formaldehyde solution (37%) with 4 L of formic acid (85%), and this mixture was heated to an internal temperature of 90° C. for 20 hours. The reaction was cooled to −5° C., and then made basic (pH>10) by addition of sodium hydroxide solution (50%). This basic liquor was then extracted 3×15 L of dichloromethane, and he combined extracts were subjected to med vacume distillation to yield crude RS-Nicotine product. This dark brown oil was high vacuum distilled twice to yield RS-Nicotine having purity that meets the requirements of the USP purity test.

What is claimed is:

1. A method of preparing (R,S)-nicotine, comprising:
reacting a nicotinate ester with N-vinyl-2-pyrrolidinone in the presence of a base and a solvent to form a first mixture; combining the first mixture with a cold acid solution to form a second mixture comprising an aqueous layer; separating the aqueous layer from the second mixture; combining the separated aqueous layer with an acid to form a third mixture; combining the third mixture with a base to form a fourth mixture comprising myosamine; reducing the myosamine to nornicotine using a reducing agent; and methylating the nornicotine to yield R,S-nicotine.

2. The method of claim 1, further comprising purifying the R,S-nicotine to yield greater than 99% pure R,S-nicotine.

3. The method of claim 1, wherein the nicotinate ester has the following formula:

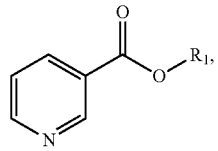

and
wherein $R_1$ is an alkyl group.

4. The method of claim 3, wherein the alkyl group is an ethyl group.

5. The method of claim 1, wherein the base is a metal hydride.

6. The method of claim 5, wherein the mole ratio of the metal hydride to the nicotinate ester is from about 1 to 4.

7. The method of claim 5, wherein the metal hydride is selected from the group consisting of lithium hydride, potassium hydride, and sodium hydride.

8. The method of claim 5, wherein the metal hydride is sodium hydride.

9. The method of claim 1, wherein the solvent is anhydrous.

10. The method of claim 1, wherein the solvent is selected from the group consisting of a dipolar aprotic amide, an ether, a polyether, an aromatic hydrocarbon, an alcohol, and combinations thereof.

11. The method of claim 1, wherein the solvent is selected from the group consisting of dimethylformamide, ethyl ether, tetrahydrofuran, glyme, diglyme, toluene, xylene, benzene, ethanol, methanol, propanol, and combinations thereof.

12. The method of claim 1, further comprising heating the first mixture to an internal temperature of 40° C. to about 110° C.

13. The method of claim 1, wherein the cold acid solution combined with the first mixture is a solution of hydrochloric acid.

14. The method of claim 13, wherein the solution of hydrochloric acid has a normality of about 3-12.

15. The method of claim 1, wherein the fourth mixture comprises a pH of 9 or greater.

16. The method of claim 1, further comprising cooling the third mixture to a temperature of about 5° C. to 10° C.

17. The method of claim 1, wherein the reducing agent is selected from the group consisting of a hydrogenation catalyst and a borohydride salt.

18. The method of claim 17, wherein the hydrogenation catalyst is palladium on carbon.

19. The method of claim 17, wherein the reducing comprises adding a solvent and the reducing agent to the myosamine to form a fifth mixture and submitting the fifth mixture to hydrogen gas.

20. The method of claim 1, wherein the methylating comprises combining the nornicotine with formic acid and formaldehyde.

\* \* \* \* \*